(12) United States Patent
Bakal

(10) Patent No.: US 6,485,435 B1
(45) Date of Patent: Nov. 26, 2002

(54) FISTULA DEVICE AND METHOD FOR IN-VIVO EVALUATION OF FISH EGG DEVELOPMENT

(75) Inventor: Robert Scott Bakal, Newnan, GA (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 24 days.

(21) Appl. No.: 09/690,714

(22) Filed: Oct. 18, 2000

(51) Int. Cl.[7] ............................................... A61B 10/00
(52) U.S. Cl. ......................................... 600/562; 600/32
(58) Field of Search ........................... 600/30, 32, 562, 600/573, 582; 604/236, 238, 327, 328, 332, 337, 338, 175; 623/23.65; 128/DIG. 25

(56) References Cited

U.S. PATENT DOCUMENTS 4,217,664 A * 8/1980 Faso ........................... 606/108
4,315,513 A * 2/1982 Nawash et al. ............. 604/537
5,658,266 A * 8/1997 Colacello et al. ........... 604/333

* cited by examiner

Primary Examiner—Kevin Shaver
Assistant Examiner—Pamela Wingood
(74) Attorney, Agent, or Firm—Ross F. Hunt, Jr.

(57) ABSTRACT

A fistula device is provided for use with fish to gather materials, e.g., eggs, from inside an exterior body wall of the fish. The fistula device includes a body member having a flange at one end thereof. The flange, in use, engages an outside surface of the exterior body wall of the fish to hold the device in place. The device also includes a hollow cylindrical body portion having both internal and external threading. A retaining ring is adapted to be placed against an interior surface of the exterior wall of the fish, and includes internal threading permitting the ring to be screwed onto the external threading of the body member. A knitted plastic mesh is secured to the retaining ring and adapted to be sutured to the inside of the exterior body wall of the fish. A removable plug used to close off the device includes a threaded portion adapted to be screwed into the body member.

11 Claims, 2 Drawing Sheets

FISTULA DEVICE AND METHOD FOR IN-VIVO EVALUATION OF FISH EGG DEVELOPMENT

FIELD OF THE INVENTION

The present invention relates to the collection and evaluation of materials such as eggs from the piscine species (i.e., fish) and, more particularly to a fistula device and method used in such collection and evaluation.

BACKGROUND OF THE INVENTION

In sturgeon culture, the currently accepted practice is to perform multiple surgical biopsies, annually, on individual fish to evaluate and collect eggs for spawning. These procedures are, understandably, extremely traumatic for the fish. The use of repeated surgical procedures causes increased trauma, pain and stress to the fish while increasing the risk of infection and contamination of samples that are collected in this manner.

Fistulas have been designed for use with cattle which allow external access to the rumen of the animal to permit removal of ingesta. A further fistula of interest is the subject of U.S. Pat. No. 5,993,485 (Beckers). This patent discloses a bladder portal including a fistula threaded on the inside to accept a seatable screw. The fistula includes a flange fitting inside the bladder and a further flange positioned outside the body. The screw is removed to permit urine to flow. U.S. Pat. No. 4,265,244 (Hill) discloses a tubular stoma adapter for insertion into the lumen of a body orifice. The adapter is held in place by tabs formed at the outer edge of a circular lip and by an adhesive sheet which holds the taps against the walls of the corresponding wall of the patient. U.S. Pat. No. 3,313,289 (Kapral) discloses a chamber for implantation into the body cavity of an animal. The chamber comprises a ring having two faces and a pair of membranes which cover the ring faces.

SUMMARY OF THE INVENTION

In accordance with the invention, a method and device are provided which enable less traumatic in-vivo evaluation of egg development within fish, and which thereby enable more efficient and less traumatic collective of roe for hatching or marketing as a consumable. The device of the invention can also be used to provide access to the ceolomic cavity for other types of sampling (i.e., biopsies of other organs, sperm collection, and the like). The device can be used by individuals involved in fish production or by researchers in fish physiology, theriogenology and medicine.

In accordance with a first aspect of the invention, a fistula device is provided for use with piscine species to gather material from inside an exterior body wall of the species, the device comprising: a body member including a flange at one end thereof adapted to engage an outside surface of the exterior body wall of the piscine species and a hollow cylindrical body portion including internal threading and external threading; a retaining ring adapted to be placed against an interior surface of the exterior wall of the species, the ring including internal threading permitting the ring to be screwed onto the external threading of the body member; a mesh member secured to retaining ring and adapted to be sutured to the exterior wall of the species internally of that wall; and a removable member including a threaded portion adapted to be screwed into the hollow body portion of said body member.

Preferably, the flange of said body member includes a plurality of holes spaced around the circumference thereof for enabling the flange to be sutured to the exterior wall of the species.

Advantageously, the retaining ring includes a plurality of holes spaced around the circumference thereof and a plurality of sutures received in the holes for affixing the mesh member to the ring. The mesh member advantageously comprises a knitted monofilament mesh, and is preferably made of polypropylene.

The member advantageously includes a flange at one end thereof.

In accordance with a second aspect of the invention, a method is provided for collecting materials from inside of a piscine species through an exterior body wall of the species, the method comprising: providing a fistula device comprising a hollow body member having a flange at one end thereof, a retaining ring having a mesh member affixed to the outer periphery thereof and a closure plug; placing the body member in a hole created by excision of skin and muscle tissue in a lateral or ventral aspect of the exterior body wall of the species, and positioning the flange of the body member against an exterior surface of the body wall of the species; placing the retaining ring inside the species through a second incision in the body wall and securing the ring to the body member; affixing the mesh member to an interior area of the body wall; and inserting the closure plug into hollow body member to close off the body member.

Preferably, the ring is threaded onto external threads on the hollow body member to secure the ring to the body member. Similarly, the closure plug is preferably threaded into an internally threaded central bore in the body member.

Advantageously, the flange of the body member is sutured to the exterior surface of the body wall of the species to provide further stability.

The mesh member is preferably affixed to the body wall by suturing the mesh member to the interior area of the body wall.

Further features and advantages of the present invention will be set forth in, or apparent from, the detailed description of preferred embodiments thereof which follows.

DESCRIPTION OF THE PREFERRED EMBODIMENTS

Figure 1:
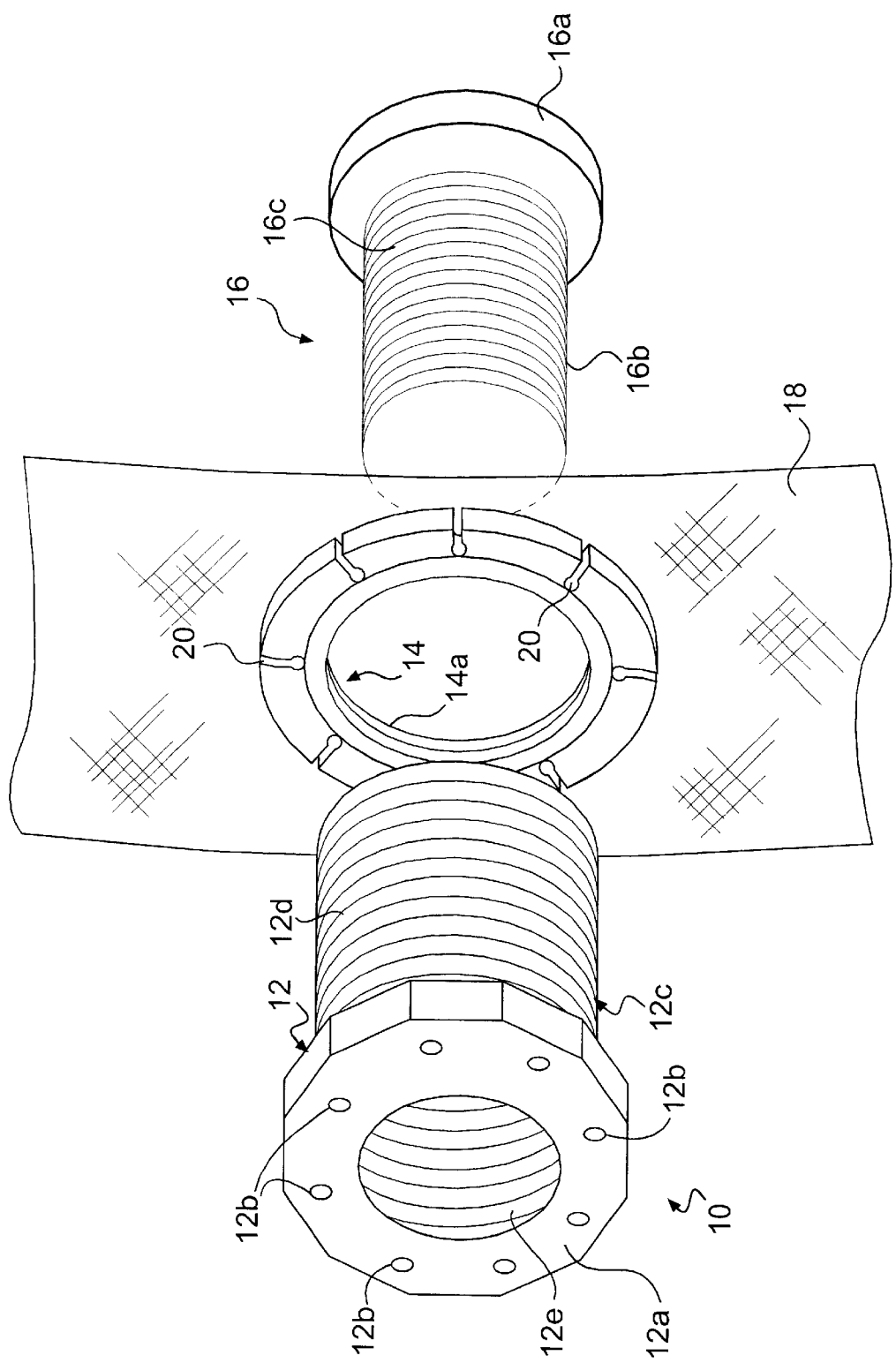
FIG. 1 is an exploded perspective view of a fistula device or apparatus constructed in accordance with a preferred embodiment of the invention.
Figure 2:
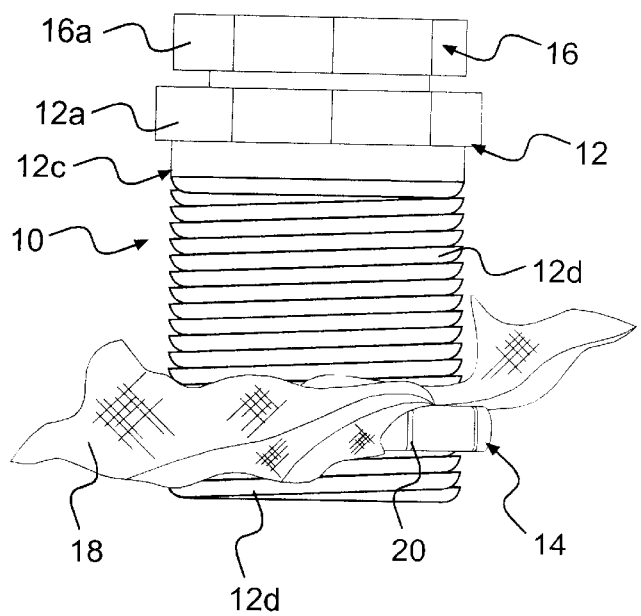
FIG. 2 is a side elevational view of the device of FIG. 1, with the components thereof assembled together.

Referring to FIGS. 1 and 2, there is shown a fistula device constructed in accordance with a preferred embodiment of the invention. The device or apparatus, which is generally denoted 10, includes a body member 12, a retaining ring 14 and a plug 16.

As can be best seen in FIG. 1, the body member 12 is generally cylindrical or tubular in shape and includes a flange 12a at one end thereof having a plurality of openings or through holes 12b equally spaced around the circumference of flange 12a. The tubular portion 12c of body member 12 includes both external threading 12d and internal threading 12e.

The retaining ring 14 includes internal threading 14a and a plurality of through holes 14b equally spaced around the circumference thereof. Holes 14b are used to enable a monofilament, knitted polypropylene mesh 18 to be sutured, by sutures indicated at 20, to ring 14.

Plug 16 includes an end flange 16a and a solid cylindrical body portion 16b having external threading 16c.

Figure 3:
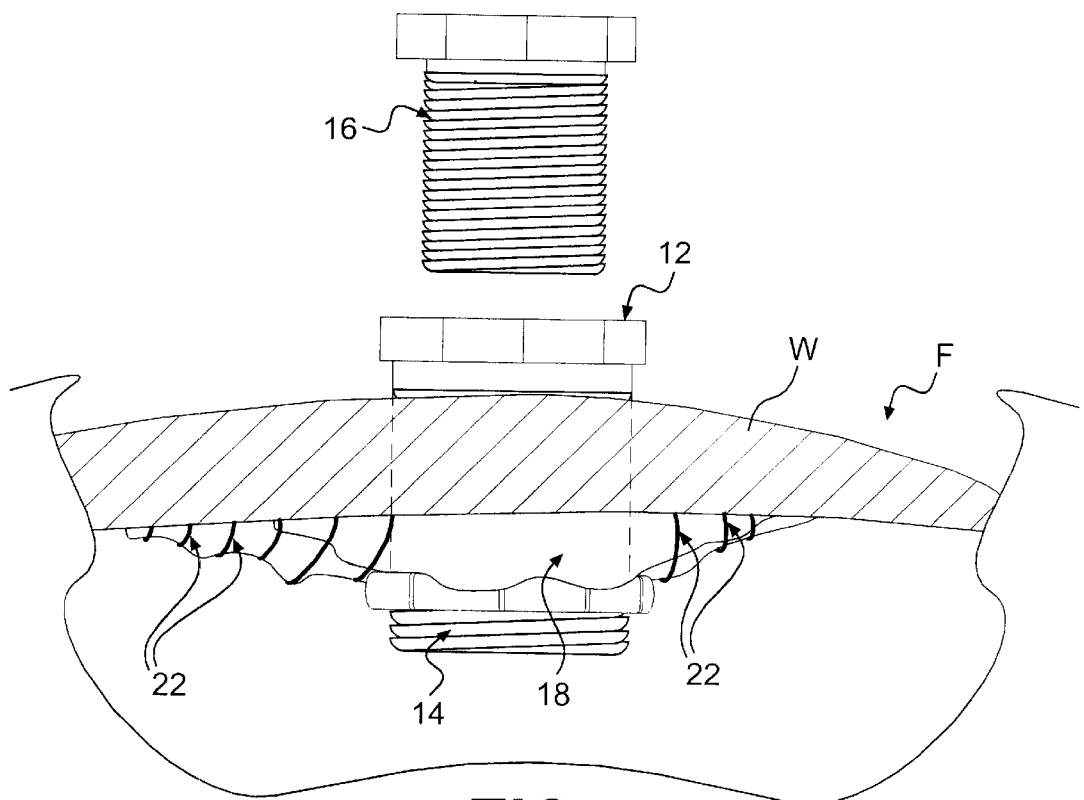
FIG. 3 is a schematic representation, in cross section, of the fistula device of the invention, in use.

Referring to FIG. 3, in use, in accordance with a preferred embodiment of the method of the invention, the body member 12 is placed through a hole, indicated generally at H in FIG. 3, created by excision of the skin and muscle tissue, in the lateral or ventral aspect of the body wall W of a fish F. The external threads 12d are designed to accept the internal threads 14a of the retaining ring 14. The retaining ring 14 is placed inside the fish F through a second incision (not shown) which is made in the ventral body wall W. The retaining ring 14 is threaded snugly onto body member 12 by means of cooperating threads 12d and 14a. The flange 12a of body member 12 is positioned on, i.e., in engagement with, the exterior of wall W as shown in FIG. 3 and provides stability to the implanted device. The fistula body member 12 can be sutured, using holes 12b in flange 12a, to the exterior wall W of fish F to provide increased stability. With ring 14 snugly in place, the mesh 18 is also sutured to the interior of body wall W, by sutures indicated at 22, and thus serves to further stabilize the device 10.

The plug 16 is threaded into the body member 12 to close off the central opening therein. The plug 16 can be removed and replaced, as needed, to take samples, harvest eggs, or other purposes.

It will be appreciated from the foregoing that device 10 can be implanted in fish so as to permit access to the ceolomic cavity without the need for additional surgical procedures. The device thus spares the fish from a great deal of trauma and pain. Further, individuals using this device can collect the necessary material (e.g., eggs) from inside the fish in an efficient manner with less risk to the fish.

Although the invention has been described above in relation to a preferred embodiment thereof, it will be understood by those skilled in the art that variations and modifications can be effected in this preferred embodiment without departing from the scope and spirit of the invention.

What is claimed:

1. A fistula device for use with piscine species to gather material from inside an exterior body wall of the species, said fistula device comprising:

a body member including a flange at one end thereof adapted to engage an outside surface of the exterior body wall of the piscine species and further comprising a hollow cylindrical body portion including internal threading and external threading;

a retaining ring adapted to be placed against an interior surface of the exterior wall of the species, said ring including internal threading permitting the ring to be screwed onto the external threading of said body member;

a mesh member secured to the retaining ring and adapted to be sutured to the exterior wall of the species internally of the exterior wall; and a removable plug member including a threaded portion adapted to be screwed into the hollow body portion of said body member.

2. A device according to claim 1 wherein said flange of said body member includes a plurality of holes spaced around the circumference thereof for enabling the flange to be sutured to the exterior wall of the species.

3. A device according to claim 1 wherein said retaining ring includes a plurality of holes spaced around the circumference thereof and a plurality of sutures received in said holes for affixing the mesh member to the ring.

4. A device according to claim 1 wherein the mesh member comprises a knitted monofilament mesh.

5. A device according to claim 4 wherein said mesh is made of polypropylene.

6. A device according to claim 1 wherein said plug member includes a flange at one end thereof.

7. A method of collecting materials from inside of a piscine species through a exterior body wall of the species, said method comprising:

providing a fistula device comprising a hollow body member having a flange at one end thereof, a retaining ring having a mesh member affixed to the outer periphery thereof, and a closure plug;

placing the body member in a hole created by excision of skin and muscle tissue in a lateral or ventral aspect of the exterior body wall of the species, and positioning the flange of the body member against an exterior surface of the body wall of the species;

placing the retaining ring inside the species through a second incision in the body wall and securing the ring to the body member;

affixing the mesh member to an interior area of the body wall; and inserting the closure plug into hollow body member to close off the body member.

8. A method according to claim 7 wherein said ring is threaded onto external threads on the hollow body member to secure the ring to the body member.

9. A method according to claim 8 wherein said closure plug is threaded into an internally threaded central bore in said body member.

10. A method according to claim 7 wherein said flange of said body member is sutured to said exterior surface of the body wall of the species.

11. A method according to claim 7 wherein said mesh member is affixed to the body wall by suturing to said interior area of said body wall.

* * * * *